United States Patent [19]
Molteno

[11] Patent Number: 4,457,757
[45] Date of Patent: Jul. 3, 1984

[54] DEVICE FOR DRAINING AQUEOUS HUMOUR

[76] Inventor: Anthony C. B. Molteno, 9 Fairfax St., Dunedin, New Zealand

[21] Appl. No.: 284,746

[22] Filed: Jul. 20, 1981

[51] Int. Cl.³ .......................................... A61M 27/00
[52] U.S. Cl. .................................................. 604/294
[58] Field of Search ................... 604/8, 9, 10, 43, 93, 604/264, 284, 294–302, 131, 173, 174, 175, 181, 268, 289, 290, 327, 317, 19

[56] References Cited

U.S. PATENT DOCUMENTS 1,246,971 11/1917 Maier .................................. 128/249
3,726,284 4/1973 Parker .............................. 128/350 R Primary Examiner—Michael H. Thaler
Attorney, Agent, or Firm—Sughrue, Mion, Zinn, Macpeak and Seas

[57] ABSTRACT

Ridged plates, concave on one side, match the curvature of the sclera of an eyeball to which they are fitted in side by side fashion. The plates each include an outwardly projecting ridge encompassing a space. A first tube extends between the plates to communicate the spaces and a second tube communicates one space through the sclera with the interior chamber of the eye.

6 Claims, 5 Drawing Figures

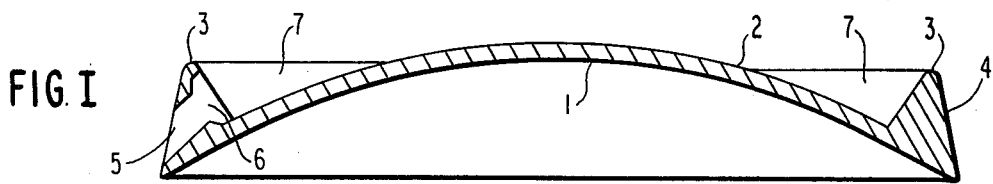
FIG. I
FIG. II
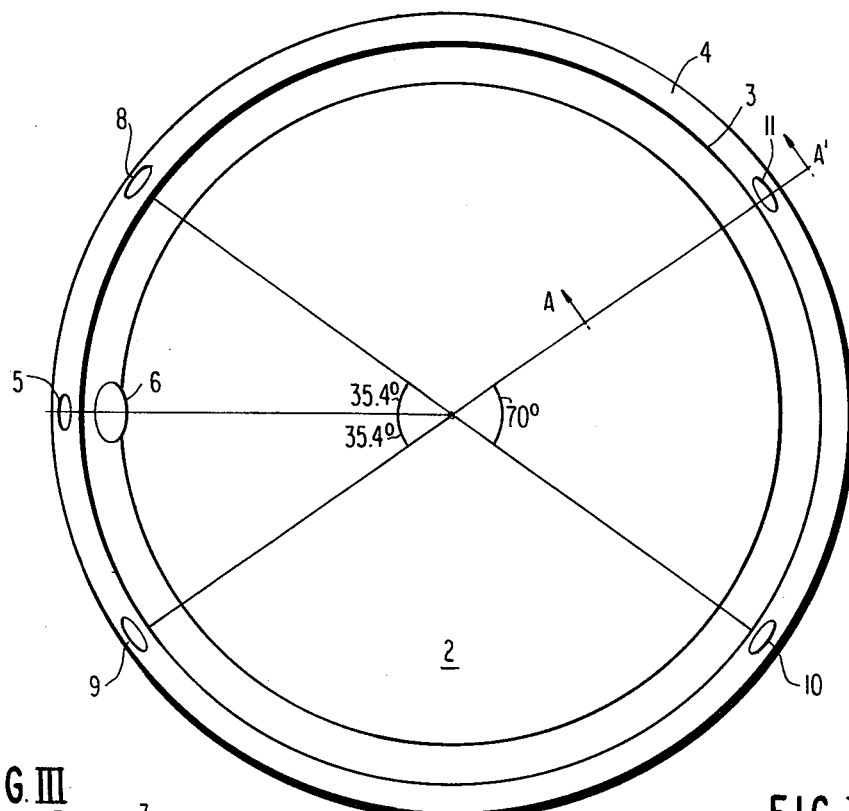
FIG. III
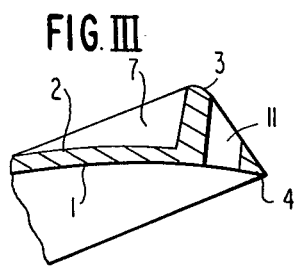
FIG. IV
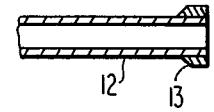
FIG. V
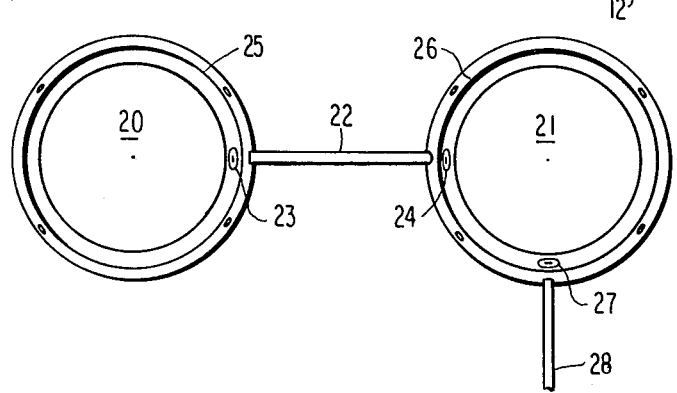

DEVICE FOR DRAINING AQUEOUS HUMOUR

This invention relates to the drainage of aqueous humour from eyes, for example in the course of research or for the relief of glaucoma.

In past practice such drainage has usually been achieved by operating to pierce the Limbus and drain off the aqueous humour into the extraocular tissue. The object of the present invention is the provision of a device which, when permanently affixed to or implanted in the eye, will allow such drainage under conditions where conventional operations are likely to fail.

The device for draining aqueous humour from an eye comprises first and second ridged bodies which are adapted for attachment to the sclera of an eye each ridged body having disposed so as to extend outwardly of the eyeball when the said attachment is made a ridge encompassing a space, a first tube extending between the ridged bodies and communicating with said spaces encompassed by the ridges, and a second tube communicating with the said space encompassed by the ridge of the first ridged body and being sufficiently long to communicate through the sclera with the anterior chamber of the eye to which the ridged bodies are attached. The ridged bodies are preferably plates having one side concavely shaped to overlie an eyeball and the other provided with a circumferential ridge. The means for attachment may be holes through the bodies for sutures and into which fibrous tissue can grow to anchor the bodies to the sclera.

More than two ridged bodies may be provided if desired, connected by tubes as described in a chain so that aqueous humour draining into the space encompassed by the ridge of the first ridged body can flow through the connecting tubes into the corresponding spaces of the other ridged bodies.

It is preferred, however, to use two ridged bodies each of the maximum size that the eye to which they are to be attached can accommodate. For an eye of similar size to a human eye, the maximum practical size for a ridged body is approximately 13.5 mm diameter, with the bodies being spaced apart 10 mm.

In the accompanying drawings:

FIG. I is a section through a ridged body constructed according to the invention;

FIG. II is a plan view of the ridged body of FIG. I;

FIG. III is a section through a part of the ridged body of FIG. I, taken of the line A—A' of FIG. II;

FIG. IV is a section through a part of a tube which is adapted for engagement with the ridged body of FIG. I; and FIG. V is a plan view of a device according to the invention in assembled form.

The parts shown in the drawing and hereinafter described are examples only of the performance of the invention and the invention is not limited to the embodiments described.

The ridged body shown in FIGS. I, II and III is drawn 10 times its actual size. The body is in the form of a circular plate which is dished to make one side 1 concave to fit the curve of an eyeball the same size as a human eye. The diameter of the plate is approximately 13 mm and the radius of curvature of the concave side 1 is 12 mm. The convex side 2 of the plate is provided with a circumferential ridge 3 of approximately 1.3 mm height. The crest of the ridge 3 is rounded and its outer face 4 is sloped at an angle of approximately 45° from the radius of curvature of the plate while the inner surface of the ridge should make an angle of approximately 90° to the upper surface of the plate.

The rim 3 is pierced by a hole 5 which may be drilled therethrough. The end portion 6 of the hole which opens into the space 7 encompassed by the ridge is widened. The main part of the hole 5 is 0.6 mm in diameter.

In the embodiment shown, the plate is intended to be sutured to the sclera of an eye, and is provided with four holes 8, 9, 10, 11 of 0.6 mm diameter to receive sutures. The holes are drilled through the ridge 3 as shown in FIG. III. After attachment fibrous tissue invades the suture holes and assists in making the attachment of the plate to the eye permanent.

FIG. IV shows a tube 12 for insertion into the hole 5 and the eye to drain aqueous humour from the eye into the space 7. The tube 12 is made of fine bore biologically inert silicone tubing. Before insertion into the hole 5, a small flange is raised at the end of the tube so as to ensure firm attachment during handling and long term attachment between tube and plate when buried in tissue fluid.

When the plates and tubes are attached to an eye, aqueous humour drains through the tubes into the spaces 7 enclosed by the ridge 3, the convex face 2 of the plate, and the overlying tissues. The intraocular pressure causes the tissues to lift and form a bleb over the plates, the blebs may become substantially hemispherical. Whilst it is possible to use only a single plate of the kind described, the total volume of bleb formed is increased, and the need for anti-inflammatory drugs to control fibrosis is reduced, by providing two or more interconnected plates. A pair of such plates is shown in FIG. V in 3 times their actual size. The plates 20, 21 are generally similar to the plate of FIG. I. A tube 22 similar to the tube 12 but of 10 mm length joins the plates through holes 23, 24 generally similar to the hole 5 and is fixed in the holes 23, 24 in the same manner as the tube 12 is fixed in the hole 5. The angle at which the holes 23 and 24 are drilled through the rims 25, 26 of the plates 20, 21 is selected for the most convenient fixing of the tube 22. The plate 21 has an additional hole 27 and tube 28, disposed at 90° around the circumference of the plate from the hole 24, which are exactly the same as the hole 5 and tube 12 of the embodiment of FIGS. I to IV.

The embodiment shown in FIG. V is for a right eye. A device for attachment to a left eye has the tube 28 attached to the plate 20. The tube 22 is preferably as short as the requirements of attachment to an eye permit in order to prevent kinking and minimize the chances of blocking. More than two plates may be provided if the conditions of use permit their attachment to the eye, interconnected by means of tubes similar to the tube 22.

What I claim is:

1. A device for draining aqueous humour from an eye comprising first and second ridged bodies which are adapted for side by side attachment to the sclera of one eye, each ridged body having disposed thereon, on the surface thereof opposite that deposited on the sclera, a ridge so as to extend outwardly of the eyeball when said attachment is made, and encompassing a space, a first tube extending between the ridged bodies and communicating with said spaces encompassed by the ridges, and a second tube communicating with said space encompassed by the ridge of the first ridged body and being sufficiently long to communicate through the sclera with the anterior chamber of the eye to which the ridged bodies are attached, said ridged bodies comprising plates each having on one side, said ridge, said plates being imperforate internally of said ridge, said plates on their other sides being concavely curved so as to closely match the sclera of an eyeball and said device being sized to fit on said sclera of said single eye.

2. A device as claimed in claim 1, characterized in that the plates are substantially circular and the ridges are raised rim portions of the plates.

3. A device as claimed in claim 1, characterized in that the ridged bodies each have a plurality of suture receiving holes through a portion thereof which is not encompassed by the said ridge.

4. A device as claimed in claim 3, characterized in that the holes are formed through the ridges of the ridged bodies so as not to communicate with the spaces encompassed by the ridges.

5. A device as claimed in claim 1, characterized in that the tubes are made of a physiologically inert material.

6. A device as claimed in claim 1, characterized in that the ridged bodies are made of physiologically inert material.

* * * * *